United States Patent
Birch et al.

(10) Patent No.: US 11,744,970 B2
(45) Date of Patent: Sep. 5, 2023

(54) AIRWAY DEVICE

(71) Applicant: KB PRO, LLC, Phoenix, AZ (US)

(72) Inventors: Cody Birch, Phoenix, AZ (US);
Thomas G. Kotoske, Phoenix, AZ (US)

(73) Assignee: KB PRO, LLC, Phoenix, AZ (US)

( * ) Notice: Subject to any disclaimer, the term of this patent is extended or adjusted under 35 U.S.C. 154(b) by 0 days.

(21) Appl. No.: 16/803,880

(22) Filed: Feb. 27, 2020

(65) Prior Publication Data

US 2021/0060275 A1 Mar. 4, 2021

Related U.S. Application Data

(60) Provisional application No. 62/892,452, filed on Aug. 27, 2019.

(51) Int. Cl.
*A61M 16/04* (2006.01)
*A61M 16/08* (2006.01)

(52) U.S. Cl.
CPC .... *A61M 16/0402* (2014.02); *A61M 16/0434* (2013.01); *A61M 16/0461* (2013.01); *A61M 16/0486* (2014.02); *A61M 16/085* (2014.02); *A61M 2230/43* (2013.01)

(58) Field of Classification Search
CPC ........ A61M 16/00; A61M 16/04–0402; A61M 16/0434; A61M 16/0816; A61M 16/0841–085; A61M 16/0486; A61M 16/0461–0463; A61M 2230/43
See application file for complete search history.

(56) References Cited

U.S. PATENT DOCUMENTS

| | | | | |
|---|---|---|---|---|
| 6,098,617 A * | 8/2000 | Connell | ............... | A61M 16/04 128/200.26 |
| 7,278,420 B2 | 10/2007 | Ganesh | | |
| 7,975,695 B2 | 7/2011 | Munn | | |
| 8,443,797 B2 * | 5/2013 | Hauge | ............... | A61M 16/0497 128/200.26 |
| 8,677,999 B2 | 3/2014 | Allum | | |
| 9,949,629 B2 | 4/2018 | Gardner | | |
| 10,040,231 B2 | 8/2018 | Nasir | | |
| 2004/0129272 A1 * | 7/2004 | Ganesh | ............... | A61M 16/085 128/207.14 |
| 2007/0017527 A1 * | 1/2007 | Totz | .................. | A61M 16/0488 128/207.15 |
| 2007/0267025 A1 * | 11/2007 | Lyons | ............... | A61M 16/0833 128/207.18 |

(Continued)

*Primary Examiner* — Rachel T Sippel
*Assistant Examiner* — Jacqueline M Pinderski
(74) *Attorney, Agent, or Firm* — Michael Best & Friedrich LLP (57) ABSTRACT

An airway adjunct or airway assembly that comprises a gas administration tube and a gas sampling tube can be utilized to improve health care to a patient. The gas administration tube may be connected, for example, to an oxygen source. The gas sampling tube may be connected, for example, to capnography equipment. Internal terminal ends of the gas administration tube and gas sampling tube can be longitudinally offset from one another within the airway assembly, which may reduce diffusion of the exhaled gas to be sampled, thereby increasing monitoring accuracy. Some embodiments of the present disclosure comprise an airway adjunct adaptable to attach into or onto various types of airway devices.

18 Claims, 6 Drawing Sheets

(56) References Cited

U.S. PATENT DOCUMENTS

| | | | |
|---|---|---|---|
| 2009/0013995 A1* | 1/2009 | Williams | A61M 16/085 |
| | | | 128/207.14 |
| 2009/0151724 A1* | 6/2009 | Wondka | A61M 16/206 |
| | | | 128/204.23 |
| 2010/0071693 A1* | 3/2010 | Allum | A61M 16/06 |
| | | | 128/203.27 |
| 2015/0099934 A1* | 4/2015 | Sartore | A61M 16/0486 |
| | | | 600/187 |
| 2017/0049985 A1* | 2/2017 | Salcedo | A61M 16/0495 |
| 2019/0125213 A1* | 5/2019 | Rockwell | A61M 16/0003 |

* cited by examiner

AIRWAY DEVICE

CROSS REFERENCE TO RELATED APPLICATION

This application claims the filing date benefit of U.S. Provisional Patent Application Ser. No. 62/892,452, filed on Aug. 27, 2019, and titled "AIRWAY ADJUNCT DEVICE," the entire contents of which are hereby incorporated by reference.

BACKGROUND

Technical Field

The present disclosure relates generally to human airway devices. In particular, this disclosure relates to medical devices for opening and/or maintaining a patient's airway.

Description of Related Art

Airway management devices are commonly used in the medical field for anesthesia and sedation cases where the healthcare provider does not use intubation or deep sedation, but where the conditions call for the patient to be semi-unconscious or unconscious during the procedure. Such airway devices include oropharyngeal airways and nasopharyngeal airways. In use, an airway device is inserted into the patient's mouth or nose, where it may help to maintain the airway free from obstruction due to relaxed airway musculature and the tongue.

In practice, airway devices have been increasingly used for procedures in office-based practice, in emergency rooms, for MRI patients, and for other cases where moderate to deep sedation with intravenous anesthetics are administered. Currently, a common practice is for healthcare providers to tape or secure tubing on, in, or near the airway device in order to analyze carbon dioxide exhaled by the patient and/or administer oxygen to the patient. However, taping or otherwise securing tubes on the airway device or the patient can be inefficient and may result in insecure or obstructive lines on or around the patient.

SUMMARY

In one embodiment, an airway adjunct is disclosed. The airway adjunct includes a gas administration tube and a gas sampling tube. The gas administration tube has a first internal terminal end and a first port. The first port is at an opposite end of the gas administration tube from the first internal terminal end. The gas sampling tube has a second internal terminal end and a second port. The second port is at an opposite end of the gas sampling tube from the second internal terminal end. The second internal terminal end is offset at least one millimeter from the first internal terminal end in a longitudinal direction away from the second port. The longitudinal direction is defined as a direction parallel to an airway flow direction of the airway adjunct.

In another embodiment, a method of maintaining a patient's airway is disclosed. The method includes providing an airway assembly and inserting the airway assembly into the patient's airway. The airway assembly includes a gas administration tube and a gas sampling tube. The gas administration tube has a first internal terminal end and a first port. The first port is at an opposite end of the gas administration tube from the first internal terminal end. The gas sampling tube has a second internal terminal end and a second port. The second port is at an opposite end of the gas sampling tube from the second internal terminal end. The second internal terminal end is offset at least one millimeter from the first internal terminal end in a longitudinal direction away from the second port. The longitudinal direction is defined as a direction parallel to an airway flow direction of the airway assembly.

In another embodiment, an airway assembly is disclosed. The airway assembly includes a housing, a gas administration tube, and a gas sampling tube. The gas administration tube has a first internal terminal end and a first port. The first port is at an opposite end of the gas administration tube from the first internal terminal end. The gas sampling tube has a second internal terminal end and a second port. The second port is at an opposite end of the gas sampling tube from the second internal terminal end. The second internal terminal end is offset at least one millimeter from the first internal terminal end in a longitudinal direction away from the second port. The longitudinal direction is defined as a direction parallel to an airway flow direction of the airway assembly.

The present disclosure will now be described more fully with reference to the accompanying drawings, which are intended to be read in conjunction with both this summary, the detailed description, and any preferred or particular embodiments specifically discussed or otherwise disclosed. This disclosure may, however, be embodied in many different forms and should not be construed as limited to the embodiments set forth herein; rather, these embodiments are provided by way of illustration only so that this disclosure will be thorough, and fully convey the full scope of the invention to those skilled in the art.

BRIEF DESCRIPTION OF THE DRAWINGS

Non-limiting and non-exhaustive embodiments of the present disclosure are described with reference to the following figures, wherein like reference numerals refer to like parts throughout the various views unless otherwise specified.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, reference is made to exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the spirit and scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

For various types of procedures, current airway devices may lack the ability to provide carbon dioxide analysis and administration of oxygen to a patient. Embodiments of the present disclosure comprise ports for carbon dioxide analysis, oxygen administration, and/or additional analysis, air administration, or other access functionalities. In various embodiments, the ports comprise sockets, apertures, connectors, or other types of openings for fluid communication.

Figure 1:
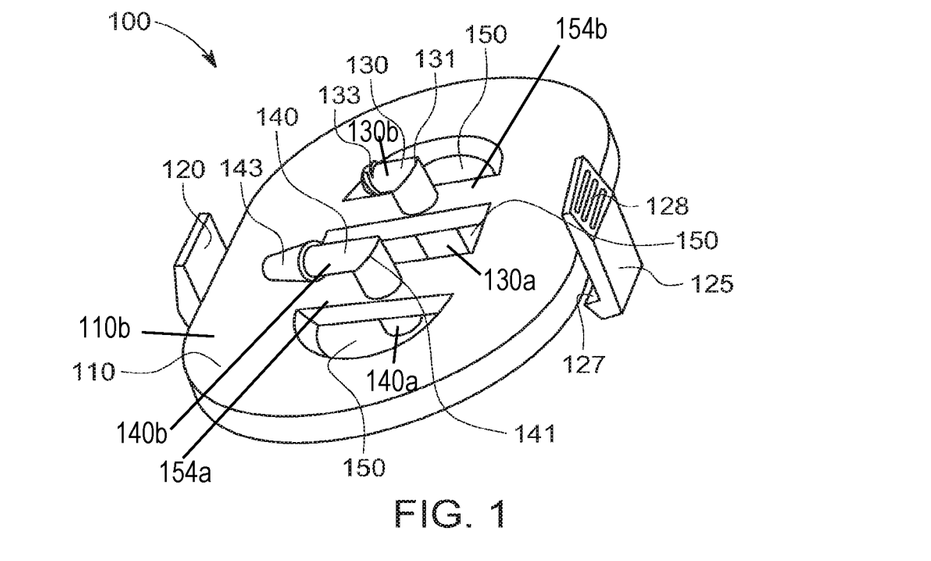
FIG. 1 is a top, perspective view of an airway adjunct according to one embodiment of the present disclosure.
Figure 2:
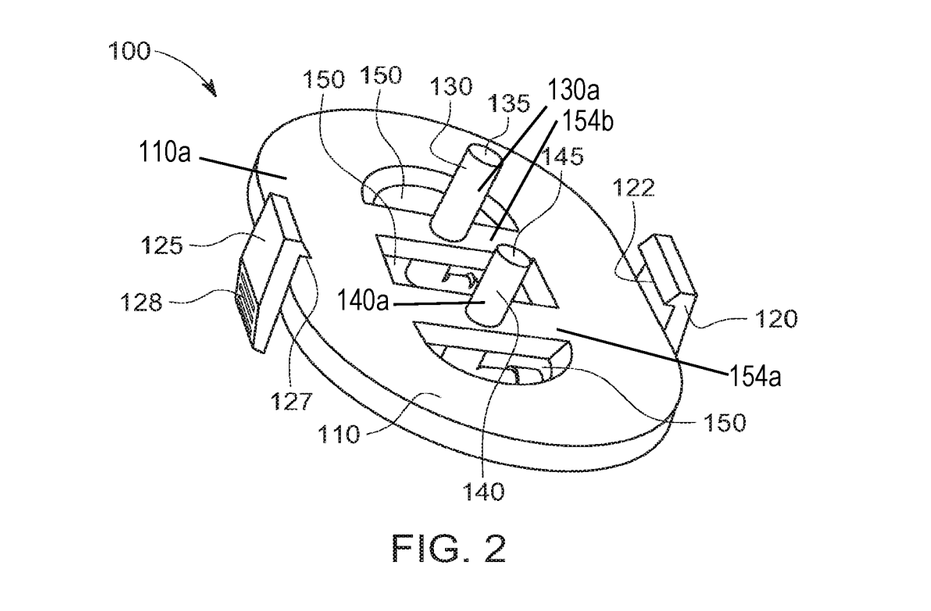
FIG. 2 is a bottom, perspective view of an airway adjunct according to embodiments of the present disclosure.
Figure 3:
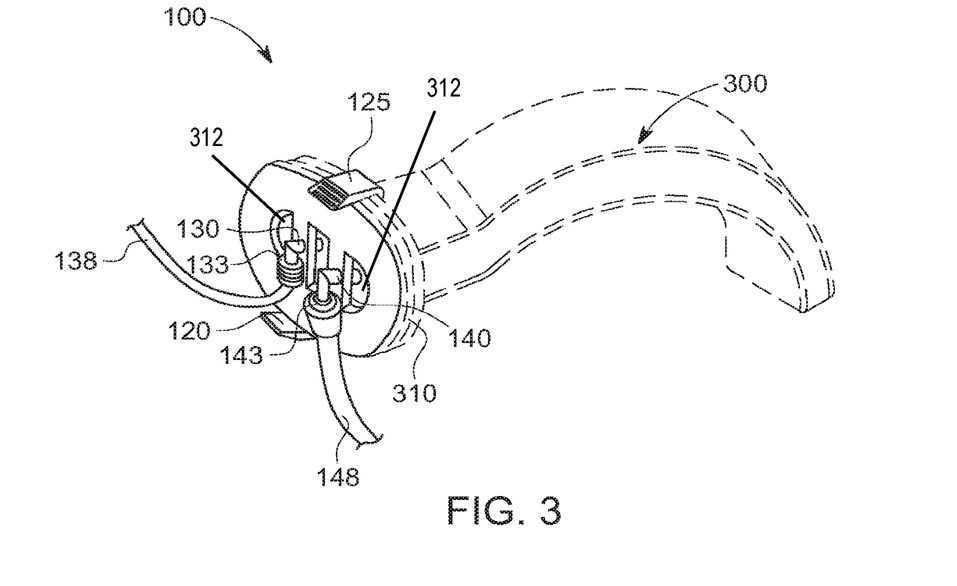
FIG. 3 depicts an airway assembly according to one embodiment of the present disclosure.

Referring to FIGS. 1-2, one embodiment of the present disclosure comprises an airway adjunct 100. In embodiments, airway adjunct 100 may be secured to an airway device (not shown in FIG. 1) to provide an exhalation gas sampling tube, a gas administration tube, and/or additional access as may be useful. In the illustrated embodiment (shown in FIGS. 3, 7, and 10), the airway device may be an oropharyngeal airway device including a collar 310 at a first end, a second end (e.g., distal end) opposite the first end, and a channel 312 (FIGS. 7 and 10) extending from the collar 310 to the second end and having an internal airway volume defined by one or more internal-facing surfaces. As shown, the channel 312 is a single continuous channel. In one embodiment, airway adjunct 100 comprises an essentially flat, disc-like body 110. In other embodiments, airway adjuncts have a body comprising a variety of shapes or geometries. In some embodiments, airway adjunct body 110 has a shape and size to approximately overlap the opening of an airway device to which the airway adjunct 100 may be attached. Some embodiments of airway adjunct 100 may include openings 150 in the body 110 to allow for ventilation through the airway adjunct 100 as the patient breathes or for insertion of suction tubing (not shown). As shown in FIGS. 1-3, in one embodiment, the body 110 includes a first surface 110a positionable adjacent to the airway device 300 (FIG. 3) and a second surface 110b opposite the first surface 110a. As shown in at least FIG. 3, the first surface 110a is configured to abut the collar 310 of the airway device. A first opening 150 extends through the body 110 and is configured to be in fluid communication with an internal airway volume of the airway device. A second opening 150 extends through the body and is configured to be in fluid communication with the internal airway volume. A third opening 150 extends through the body and is configured to be in fluid communication with the internal airway volume. A first cross-member 154a extends between the first opening 150 and the second opening 150, and a second cross-member 154b extends between the second opening 150 and the third opening 150. As shown, the first cross-member 154a is spaced apart from the second cross-member 154b by a distance, which in this case is the width of the second opening 150. Also, the first cross-member 154a is oriented parallel to the second cross-member 154b. Each of the openings 150 extend between the first surface 110a and the second surface 110b. Moreover, each of the openings has a first side and a second side that is opposite the first side. Each of the first cross-member 154a and the second cross-member 154b extend between the first side and the second sides of the respective openings 150. When the airway adjunct 100 is coupled to the airway device 300, the first cross-member 154a and the second cross-member 154b are each spaced apart from the channel 312. In other words, neither the first cross-member 154a nor the second cross-member 154b extend into the channel 312.

Embodiments of airway adjunct 100 comprise clamping tabs 120, 125 that extend from the body 110 and are adapted to secure airway adjunct 100 to an airway device. In one embodiment, clamping tabs 120, 125 can provide a clamping force onto an airway device to which airway adjunct 100 is secured. In one embodiment, clamping tabs 120, 125 comprise a corresponding inner-facing step 122, 127 (shown in FIG. 2) to secure to an annular rim on an airway device and maintain airway adjunct 100 positioned on said airway device. In embodiments, clamping tabs 120, 125 are adapted to flex, with the stepped end flexing outward as airway adjunct 100 is affixed to and/or removed from the airway device. Embodiments of clamping tabs 120, 125 comprise knurled surface 128 to provide grip as a user squeezes clamping tabs 120, 125 in order to move stepped ends outward to release steps 122, 127 from the annular rim on an airway device and thereby remove airway adjunct 100 from said airway device.

Embodiments of airway adjunct 100 comprise a gas sampling tube 130 and gas administration tube 140. In the embodiment of FIGS. 1-3, the gas sampling tube 130 extends through the first cross-member 154a. Moreover, as shown in the illustrated embodiments, the gas sampling tube 130 includes a first portion 130a that is in fluid communication with a second portion 130b. With specific reference to FIGS. 1-3, the first portion 130a extends through the first cross-member and is oriented perpendicular to the first surface 110a, while the second portion 130b is oriented parallel to the second surface 110b. The first portion 130a is therefore positioned between the first opening 150 and the second opening 150. In various embodiments, gas sampling tube 130 comprises port 133. In embodiments, port 133 is located at a distal end of gas sampling tube 130. Embodiments of port 133 comprise a connector compatible for carbon dioxide monitoring, such as a T-Connector or Luer-style connector, or other types of connectors and/or tubing that may be used with capnography equipment. In other embodiments, port 133 is adapted to provide access for other types of expiration monitoring equipment or devices.

In various embodiments, port 133 is adapted to connect to a tubing, hose, and the like to provide fluid communication from gas sampling tube 130 to a carbon dioxide monitoring machine (not shown). According to various embodiments, the carbon dioxide monitoring machine monitors exhaled carbon dioxide via the gas sampling tube 130. For example, the carbon dioxide monitoring machine may comprise an end-tidal carbon dioxide monitoring machine. In various embodiments, port 133 connects directly or indirectly to an apparatus adapted to measure a partial pressure of carbon dioxide and/or maximal concentration of carbon dioxide at the end of an exhaled breath. According to various embodiments, monitoring equipment connected to port 133 may be utilized to measure vital signs of the patient.

In the embodiment of FIGS. 1-3, the gas administration tube 140 extends through the second cross-member 154b. Moreover, as shown in the illustrated embodiments, the gas administration tube 140 includes a third portion 140a that is in fluid communication with a fourth portion 140b. With specific reference to FIGS. 1-3, the third portion 140a extends through the second cross-member 154b and is oriented perpendicular to the first surface 110a, while the fourth portion 140b is oriented parallel to the second surface 110b. The third portion 140a is therefore positioned between the second opening 150 and the third opening 150. In some embodiments, gas administration tube 140 comprises port 143. In embodiments, port 143 is located at a distal end of gas administration tube 140. Embodiments of port 143 comprise a connector compatible for administration of oxygen or other gas to be administered to a patient. Embodiments of port 143 are adapted to connect to tubing that may connect to an oxygen source.

In embodiments of the present disclosure, tubes 130, 140 each include an elbow bend 131, 141 of approximately ninety degrees. The elbow bends 131, 141 are located between the respective portions 130a, 130b, 140a, 140b of the tubes 130, 140. According to other embodiments, elbow bends have angles other than ninety degrees. Some embodiments of airway adjunct 100 comprise tubes 130, 140 having no bend. In embodiments, elbow bends 131, 141 are situated such that when airway adjunct 100 is attached to and/or inserted within an airway device in a patient's airway, ports 133, 143 are directed toward the patient's chin or the patient's nose. In other embodiments, elbow bends 131, 141 are angled laterally, to the side of the patient's face. In other embodiments, elbow bends 131, 141 are angled at a combination of lateral and medial directions. In some embodiments, elbow bends 131, 141 do not comprise mutually corresponding angles.

Referring to FIG. 2, embodiments of airway adjunct 100 comprise internal terminal ends 135, 145 of tubes 130, 140, respectively. According to embodiments, exhaled carbon dioxide and/or other exhaled gases may pass into internal terminal end 135, through gas sampling tube 130, through a tube connected thereto via port 133, and into a gas sampling machine as described above. In some embodiments, oxygen or other gas administered to a patient may flow from a gas source such as one or more tanks, through a supply tube, into gas administration tube 140 via port 133, out internal terminal end 145, and into the patient's airway.

Embodiments of the present disclosure include internal terminal ends 135, 145, each positioned centrally relative to the internal airway volume of the single continuous channel such that they are configured to be spaced apart from the internal-facing surfaces of the single continuous channel. Each of the internal terminal ends 135, 145 also define defining a different end position of tubes 130, 140. Throughout the present disclosure, the respective lengths of tubes 130, 140 leading to internal terminal ends 135, 145 may be defined in relation to the body 110. For example, in the illustrated embodiments, the internal terminal end 145 is spaced apart from the first surface 110a by a first distance and the internal terminal end 135 is spaced apart from the first surface 110a by a second distance that is greater than the first distance. Throughout the present disclosure, the respective lengths of tubes 130, 140 leading to internal terminal ends 135, 145 may be defined in a relative sense by comparing the distance between each internal terminal end 135, 145, regardless of the actual length of tubes 130, 140. Such a measurement of the distance between the internal terminal ends 135, 145 may be made along a line parallel to one or both tubes 130, 140 near their respective internal terminal ends 135, 145. In other words, a statement that internal terminal end 135 is approximately one millimeter longer than internal terminal end 145 can be interpreted to mean that internal terminal end 135 extends approximately one millimeter farther into the patient's airway and/or into an airway device to which airway adjunct 100 is attached. Alternatively, the respective length of each internal terminal end 135, 145 may be defined as a distance that the respective portions of tubes 130, 140 extend from body 110.

In embodiments, a difference in position between internal terminal ends 135, 145 may allow the patient's exhaled breath to be sampled more accurately due to reduced diffusion with the oxygen and/or other gas administered from gas administration tube 140 via internal terminal end 145. In some embodiments, internal terminal end 135 extends farther into the patient's airway than internal terminal end 145, so that administered oxygen or other gas exiting from internal terminal end 145 might not mix with the patient's exhaled breath, or may only minimally mix therewith.

According to some embodiments, the positional differential between internal terminal ends 135 and 145 is defined as a ratio between the respective tubes 130, 140. For example, in one embodiment, the portion of tube 130 between body 110 and internal terminal end 135 is fifty percent longer than the corresponding length of tube 140 between body 110 and internal terminal end 145. In the present disclosure, the respective portions of tubes 130, 140 between body 110 and respective internal terminal ends 135, 145 may be referred to as the "interior portion." In other examples, the interior portion of tube 130 is forty to sixty percent longer than the interior portion of tube 140. In other examples, the interior portion of tube 130 is thirty to forty percent longer than the interior portion of tube 140. In other examples, the interior portion of tube 130 is at least ten percent longer than the interior portion of tube 140. In other examples, the interior portion of tube 130 is at least five percent longer than the interior portion of tube 140.

According to some embodiments, the positional differential between internal terminal ends 135 and 145 is defined as an absolute offset difference therebetween. For example, in one embodiment, internal terminal end 135 is offset approximately one millimeter from internal terminal end 145. In other examples, internal terminal end 135 is offset approximately one to two millimeters from internal terminal end 145. In other examples, internal terminal end 135 is offset approximately two to four millimeters from internal terminal end 145. In other examples, internal terminal end 135 is offset at least approximately one millimeter from internal terminal end 145. In the present disclosure, the term "approximately" may refer to a range within ten percent of the stated value.

Various embodiments of the present disclosure are adapted to removably attach to an airway device to form an airway assembly. FIG. 3 depicts airway adjunct 100 attached to an oropharyngeal airway device 300. Various embodiments are adapted to attach to and/or on a variety of types of airway devices. In various embodiments, tube 138 may provide communication from gas sampling tube 130 to a gas sampling device. In various embodiments, tube 148 may provide communication from an administered gas source, such as an oxygen tank or supply line, to gas administration tube port 140.

While airway adjunct 100 is attached to an oropharyngeal airway device 300 as shown in FIG. 3, interior portions of tubes 130, 140 extend into the body or housing of the airway device. Clamping tabs 120, 125 secure airway adjunct 100 to collar 310 of oropharyngeal airway device 300.

Figure 4:
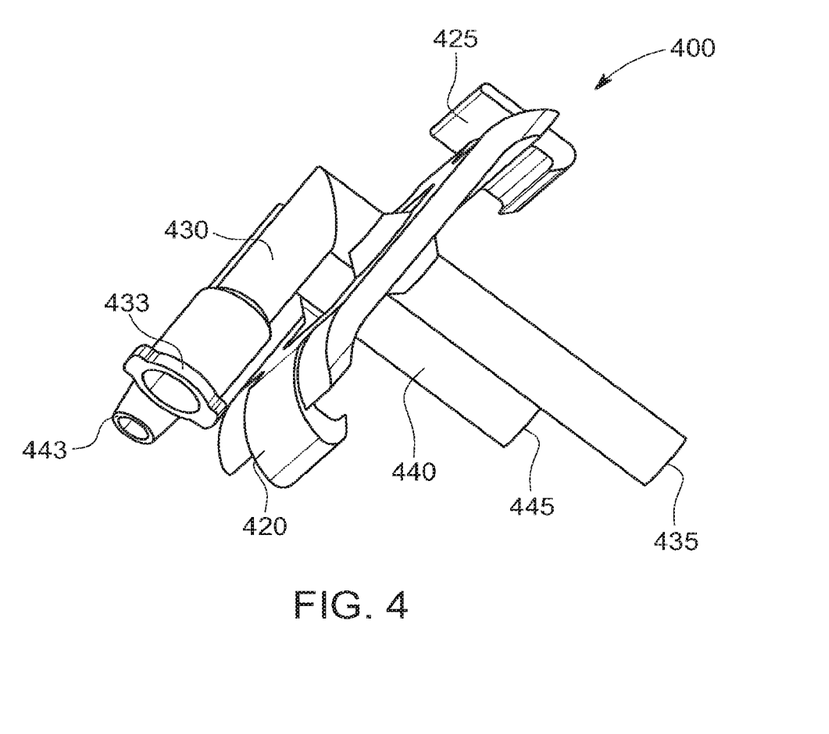
FIG. 4 is a side, perspective view of an airway adjunct according to another embodiment of the present disclosure.
Figure 5:
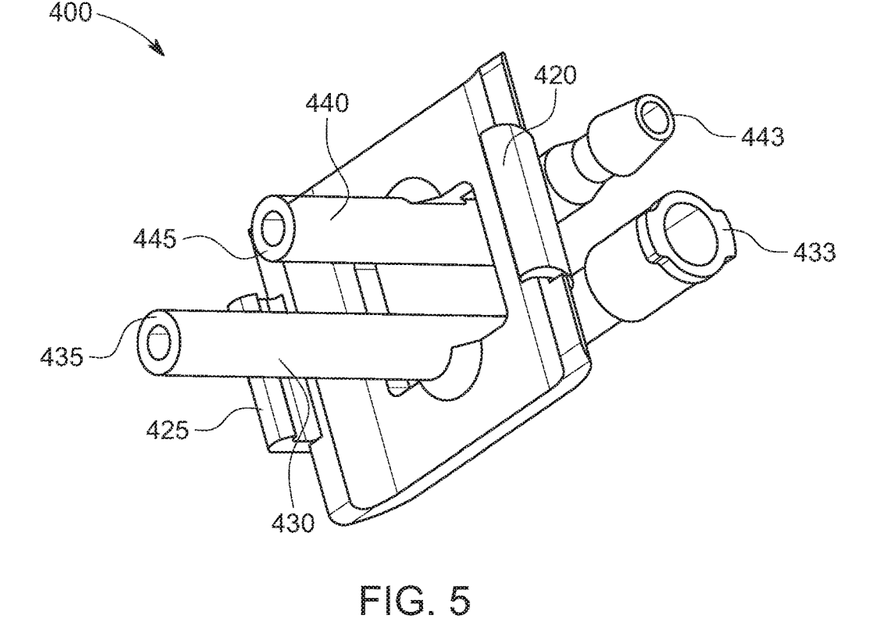
FIG. 5 is a bottom, perspective view of an airway adjunct according to another embodiment of the present disclosure.
Figure 6:
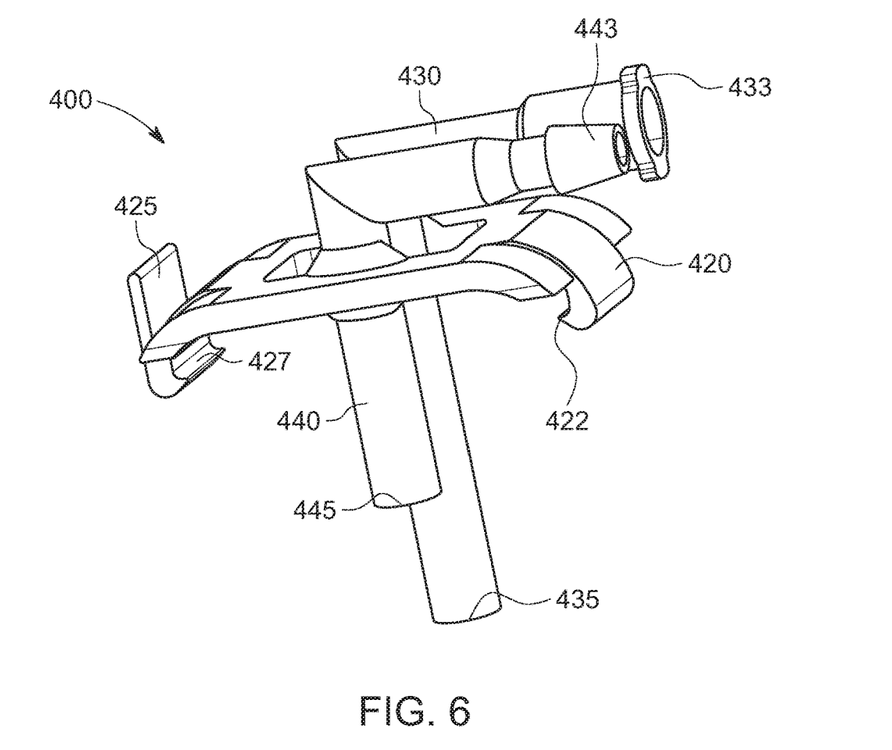
FIG. 6 is a reverse, side perspective view of an airway adjunct according to another embodiment of the present disclosure.

Referring to FIGS. 4-6, one embodiment of an airway adjunct 400 is depicted. As set forth above with respect to airway adjunct 100, airway adjunct 400 comprises gas sampling tube 430 and gas administration tube 440. In embodiments, gas sampling tube 430 comprises port 433 and internal-facing end 435. In embodiments, gas administration tube 440 comprises port 443 and internal facing end 445.

One embodiment of airway adjunct 400 comprises clamping tabs 420, 425. In embodiments, clamping tabs 420, 425 comprise a corresponding inner-facing step 422, 427 to secure to an annular rim on an airway device and maintain airway adjunct 400 positioned on said airway device. In embodiments, clamping tab 425 is adapted to flex, with the stepped end flexing outward as airway adjunct 400 is affixed to and/or removed from the airway device. Embodiments of clamping tab 425 comprise a knurled surface (not shown) to provide grip as a user squeezes clamping tab 425 in order to move inner-facing step 427 outward to release steps 422, 427 from the annular rim on an airway device and thereby remove airway adjunct 400 from said airway device.

Figure 7:
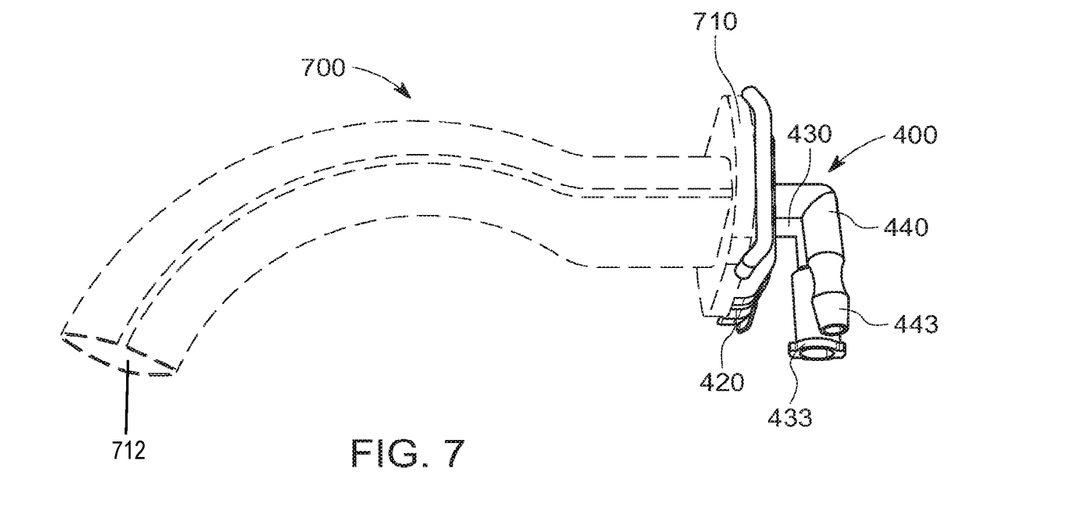
FIG. 7 depicts an airway assembly according to another embodiment of the present disclosure.

FIG. 7 depicts airway adjunct 400 attached to an oropharyngeal airway device 700, thereby forming an airway assembly. As shown, airway adjunct 400 is held to oropharyngeal airway device 700 by clamping tabs 420, 425 secured to rim 710 or collar of oropharyngeal airway device 700. In the configuration depicted in FIG. 7, internal-facing ends 435, 445 terminate within the body of oropharyngeal airway device 700.

Figure 8:
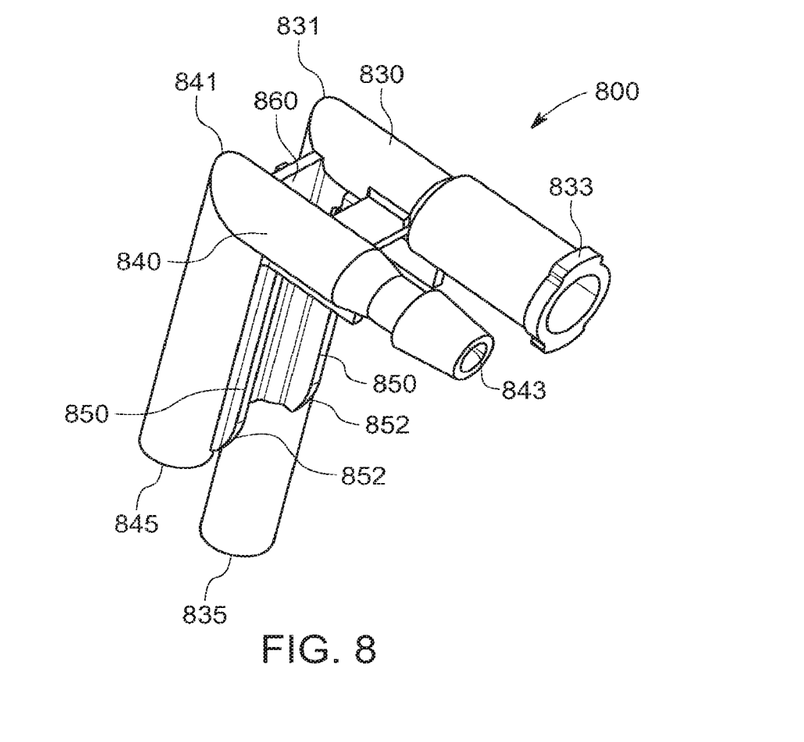
FIG. 8 is a front, perspective view of an airway adjunct comprising tubes joined by a web according to one embodiment of the present disclosure.
Figure 9:
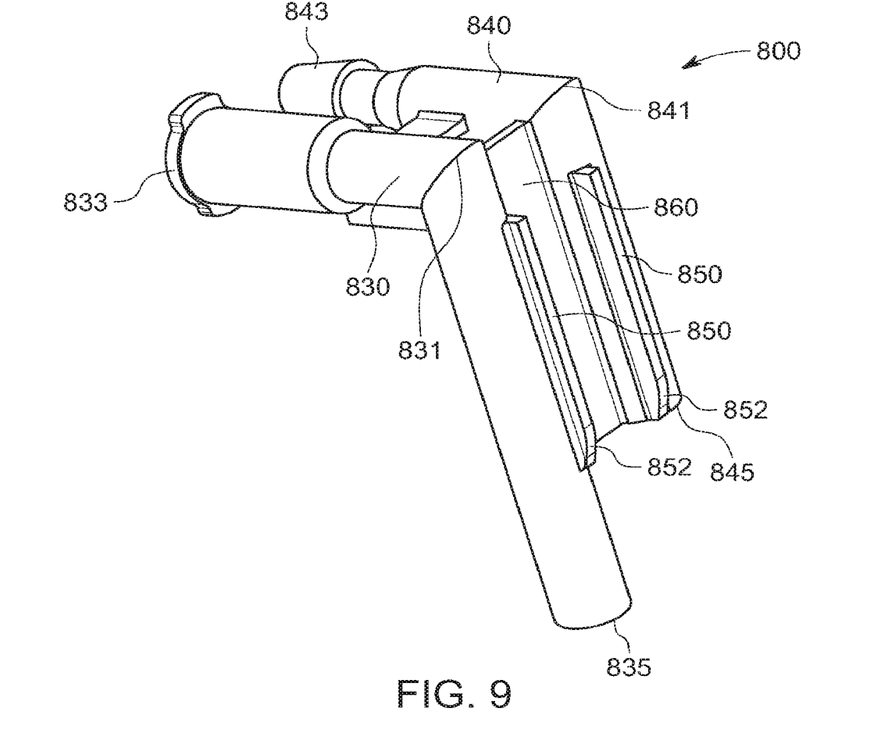
FIG. 9 is a rear perspective view of an airway adjunct comprising tubes joined by a web according to one embodiment of the present disclosure.

Referring to FIGS. 8-9, one embodiment of an airway adjunct 800 comprises gas sampling tube 830 and gas administration tube 840. According to embodiments, gas sampling tube 830 comprises a port 833 and an internal terminal end 835. According to embodiments, gas administration tube 840 comprises a port 843 and an internal terminal end 845.

In embodiments, internal terminal ends 835, 845, each comprise a different longitudinal position as set forth above with respect to internal terminal ends 135, 145. As depicted in FIGS. 8-9, gas sampling tube 830 and gas administration tube 840 are connected by web 860. According to various embodiments, web 860 has sufficient rigidity to hold gas sampling tube 830 and gas administration tube 840 in a spaced relationship relative to each other. Embodiments of airway adjunct 800 comprise ridges 850 on gas sampling tube 830 and gas administration tube 840, wherein ridges 850 have a sufficient size to allow airway adjunct 800 to snugly fit within the throat of an airway device. In some embodiments, ridges 850 comprise tapered ends 852, which may ease insertion of airway adjunct 800 into an airway device. Some embodiments comprise one or more ridges on web 860.

Various embodiments of airway adjunct 800 have elbow bends 831, 841 in gas sampling tube 830 and gas administration tube 840. In some embodiments, elbow bends 831, 841 comprise an angle of approximately ninety degrees. In other embodiments, elbow bends 831, 841 comprise angles of various other degrees as may be desirable.

Figure 10:
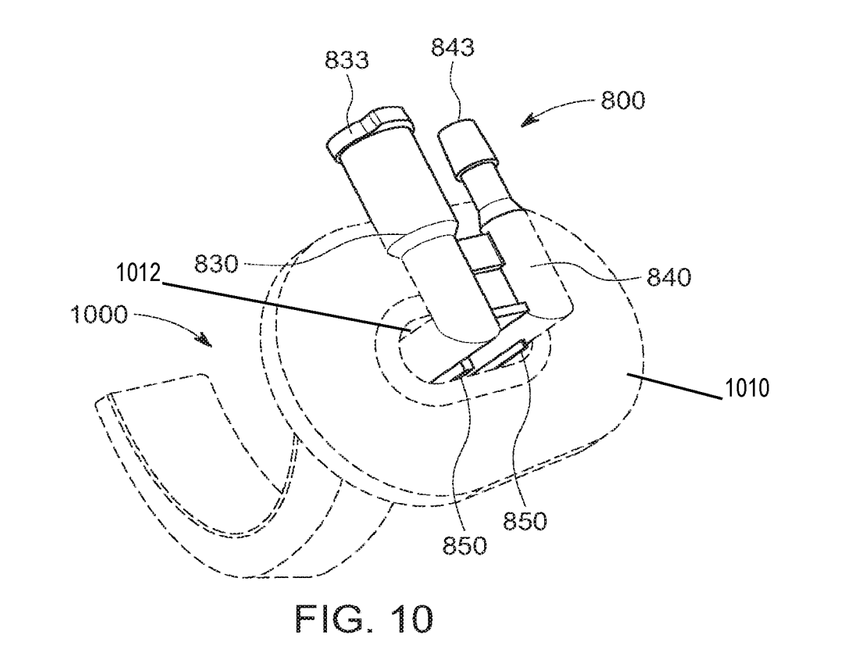
FIG. 10 depicts an airway assembly comprising an airway adjunct inserted into an airway device.

As shown in FIG. 10, airway adjunct 800 may be seated within an oropharyngeal airway device 1000 to form an airway assembly. In embodiments, airway adjunct 800 may be held within the throat of oropharyngeal airway device 1000 by a friction fit between ridges 850 and a corresponding internal surface of oropharyngeal airway device 1000. In other embodiments, airway adjunct 800 lacks ridges but may be held in place within oropharyngeal airway device 1000 by a friction fit between various external-facing surfaces of airway adjunct 800 and corresponding internal-facing surfaces of oropharyngeal airway device 1000.

According to embodiments of the present disclosure, an airway adjunct may be adapted to fit a variety of oropharyngeal airway device types. As would be understood by a person of ordinary skill in the art having the benefit of this disclosure, airway adjuncts may comprise clamping tabs and/or friction fit surfaces as set forth above, adapted to fit throat diameters and/or internal shapes of different airway devices. Further, one airway adjunct embodiment may comprise clamping tabs and/or friction fit surfaces adapted to fit multiple different airway device collar sizes and/or shapes. As such, a single airway adjunct design or size may be stocked in a hospital or other operating facility, the single design or size being capable of universally fitting multiple different types or sizes of airway devices.

The present disclosure is not limited to clamping tabs for attaching adjunct devices to an airway device as described above. In other embodiments, the adjunct device is attached and/or fastened to an airway device in various other fashions. For example, some embodiments of an adjunct device are secured to an airway device by the use of magnets. Other embodiments secure to an airway device by hook-and-loop fasteners. Other embodiments secure to an airway device by a tongue-and-groove configuration.

In embodiments, the airway adjunct device is made of polyvinyl material. In other embodiments, that the airway is manufactured from other materials and compounds thereof that may be appropriate for medical airway devices.

As depicted above, embodiments of airway adjunct devices have tubes with an external elbow bend. In other embodiments, one or more tubes have no such bends, but instead comprise a relatively straight section extending from the airway adjunct device body to a port. In other embodiments, the ports have other shapes and/or orientations as may be called for in various situations and circumstances. Some embodiments may include, in addition to a gas administration tube and a gas sampling tube, other tubes and/or ports providing other access as may be useful.

Figure 11:
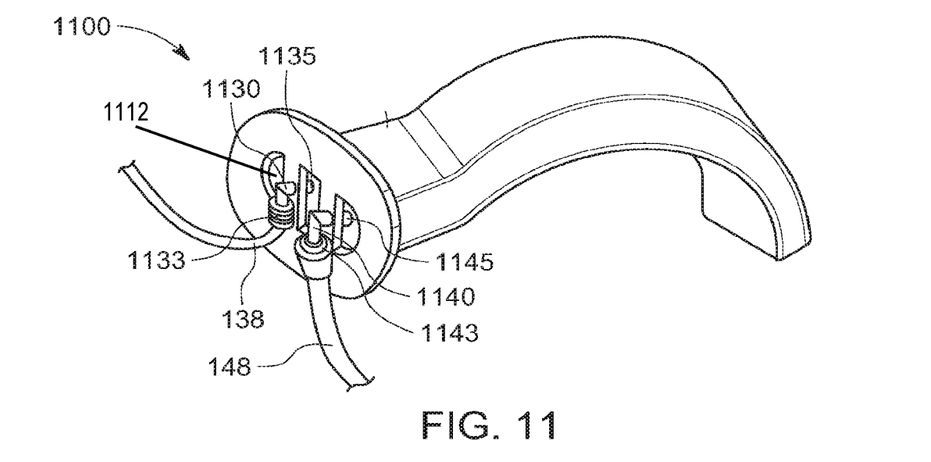
FIG. 11 depicts an integral airway device comprising ports according to one embodiment of the present disclosure.

Referring to FIG. 11, embodiments of the present disclosure comprise an integral airway assembly 1100 having a gas sampling tube 1130 and a gas administration tube 1140. According to some embodiments, airway assembly 1100 comprises a single-piece component including both an airway adjunct portion and an airway device portion. In some examples, a single-piece airway assembly 1100 is manufactured as an integrally formed component. In other embodiments, an airway assembly 1100 comprises multiple separate components that may be permanently or separably joined. In one embodiment, gas sampling tube 1130 comprises port 1133. In one embodiment, gas administration tube 1140 comprises port 1143 In various embodiments, gas sampling tube 1130 and gas administration tube 1140 each comprise a respective hollow tubular element providing fluid communication between ports 1133, 1143 and corresponding internal terminal ends 1135, 1145. In embodiments, internal terminal ends 1135, 1145 terminate within housing 1110 of airway assembly 1100.

According to various embodiments, internal terminal ends 1135, 1145 are longitudinally offset from each other. As set forth above with respect to internal terminal ends 135, 145, in embodiments of the present disclosure, internal terminal end 1135 extends farther into the central cavity of housing 1110 than internal terminal end 1145. In some embodiments, the longitudinal offset between internal terminal end 1135 and internal terminal end 1145 is defined as an absolute difference as set forth above with respect to internal terminal ends 135, 145. In some embodiments, the longitudinal offset between internal terminal end 1135 and internal terminal end 1145 is defined as a relative difference as set forth above with respect to interior portions of tubes 130, 140. In embodiments shown and described in the present disclosure, and other embodiments that fall within the scope thereof, internal terminal ends 1135, 1145 may be longitudinally offset from each other.

Throughout the present disclosure, the term "longitudinal" may be defined as a direction parallel to the patient's airway flow. In other words, an airway flow direction is parallel to an airway device that is inserted, may be inserted, or has been inserted into a patient's airway. Particularly, the airway flow direction may be defined by the direction of bulk movement of air through a patient's internal respiratory pathway at or around the pharynx. Thus, the airway flow direction can be applied to describe the ports and tubing of an airway adjunct, even while the airway adjunct is not inserted into an airway device, based on the intended and designed orientation of insertion into an airway device.

Some embodiments of the present disclosure comprise airway adjunct devices that are adapted to fit a nasopharyngeal airway. Such embodiments are adapted to allow a healthcare provider to fasten the airway adjunct to the airway and thereby administer oxygen, analyze carbon dioxide and/or additional analysis, or complete other access functions as may be appropriate.

In operation, a healthcare provider may utilize an embodiment of an airway device or an airway adjunct during a medical procedure where it may be desirable to monitor a patient's carbon dioxide or other exhaled gases. Additionally or alternatively, a healthcare provider may utilize an embodiment of an airway device or an airway adjunct during a medical procedure where it may be desirable to administer oxygen or other administered gas to the patient.

According to various embodiments, a healthcare provider can insert an airway device, such as an oropharyngeal airway device or a nasopharyngeal airway device, into a patient's airway following standard practices and procedures. Thereafter, the healthcare provider may secure an airway adjunct to the airway device. In alternative embodiments, the adjunct device may be secured to the airway device prior to insertion into the patient's airway. As set forth above, the airway adjunct may be secured to the airway device by a friction fit, by clamping tabs, magnets, hook-and-loop, tongue-and-groove, or other mechanisms as known in the art or not yet known in the art. In some embodiments, the healthcare provider may insert an integral airway assembly into the patient's airway, the airway assembly having a gas sampling tube and a gas administration tube.

Under some circumstances, it may be desirable for ports of the airway adjunct to point downward (i.e., toward the patient's chin). For example, a medical procedure may involve treating a portion of the patient's face above the mouth and for reasons of efficiency or convenience of the healthcare provider, and to mitigate interference and/or obstruction from tubes and ports, it may be desirable for tubing connected to the airway to be directed away from the target area on the patient. In such cases, the healthcare provider may attach the airway adjunct to the airway device with the appropriate orientation. In other cases, it may be desirable for ports of the airway adjunct to point upward (i.e., toward the patient's nose). The healthcare provider may likewise attach the airway adjunct to the airway device with the appropriate orientation. In some cases, it may be desirable to switch the orientation of the ports partway through a medical procedure, which the healthcare provider may do. In some embodiments, the airway adjunct may be removed from the airway device by pushing or squeezing clamping tabs (or otherwise released the airway adjunct from the airway device) and pulling the airway adjunct away from the airway device. In other embodiments that do not include clamping tabs, the airway adjunct may be removed from the airway device by pulling the airway adjunct away from the airway device.

Upon insertion of the airway device or airway assembly and/or attachment of the airway adjunct, the healthcare provider may connect one or more ports of the airway adjunct or airway assembly to corresponding tubes. For example, a gas sampling tube of the airway adjunct or airway assembly may be connected to a gas sampling tube connected to expiration monitoring equipment such as a capnography equipment. A gas administration tube may be connected to a supply such as an oxygen supply line or oxygen tank.

Under some circumstances, it may be desirable to use an airway adjunct during a portion of a medical procedure. In such cases, the adjunct device can be inserted in place on the airway device or removed at any time during the procedure.

According to various embodiments of the present disclosure, the relative positions of internal terminal ends may affect the accuracy of exhaled gas monitoring and data gathering. For example, embodiments of the present disclosure comprise an airway assembly that has a gas sampling tube that extends farther into the body of the airway assembly than a gas administration tube. Such embodiments may undergo reduced diffusion of the patient's exhalation with administered gas compared to an airway having both ports at the same longitudinal position.

Figure 12:
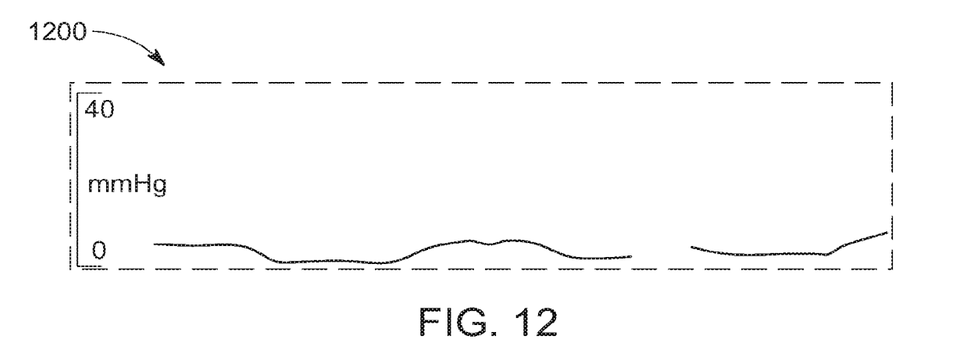
FIG. 12 is a depiction of a carbon dioxide waveform where an airway device has a gas sampling port that is approximately even with an oxygen administration port.

Referring to FIG. 12, a carbon dioxide waveform 1200 for a patient's exhalation is depicted. Waveform 1200 represents carbon dioxide monitored using an airway having respective internal terminal ends of an oxygen administration tube and a gas sampling tube port that are approximately even with each other within the airway assembly.

Figure 13:
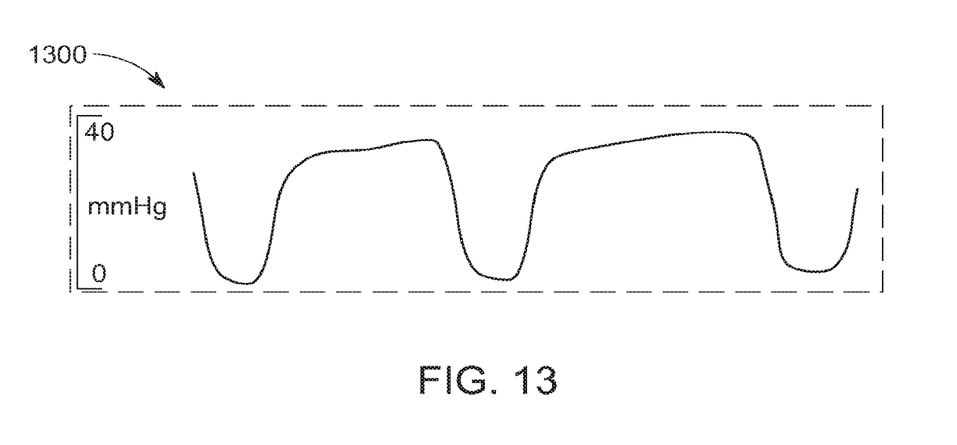
FIG. 13 is a depiction of a carbon dioxide waveform where an airway device has a gas sampling port that is longitudinally offset from an oxygen administration port according to various embodiments of the present disclosure.

Referring to FIG. 13, a carbon dioxide waveform 1300 for a patient's exhalation is depicted. Waveform 1300 represents carbon dioxide monitored using an airway having an internal terminal end of a gas sampling tube that extends at least one millimeter farther into the airway assembly than an internal terminal end of a gas administration port.

As can be seen by comparing waveform 1200 with waveform 1300, carbon dioxide waveform 1200 is relatively dampened. It is theorized that diffusion with administered oxygen gas thus affected waveform 1200 and reduced the data resolution thereof.

As would be understood by a person of ordinary skill in the art having the befit of this disclosure, in office-based or ambulatory surgery, or other settings where minimally invasive anesthesia may be preferred, embodiments of the present disclosure may assist healthcare providers in administering oxygen, anesthesia, and/or additional substances to a patient while allowing for the collecting of exhalation for measuring and monitoring thereof.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the spirit and scope of the present disclosure.

What is claimed is:

1. An airway adjunct adapted to secure to an airway device, the airway device having a first end, a second end opposite the first end, and an internal airway volume defined by a single continuous channel with one or more internal-facing surfaces extending from the first end to the second end, the airway adjunct comprising:
    a body that is configured to be removably coupled to the first end of the airway device, the body including
        a first opening extending through the body and configured to be in fluid communication with the internal airway volume,
        a second opening extending through the body and configured to be in fluid communication with the internal airway volume,
        a third opening extending through the body and configured to be in fluid communication with the internal airway volume,
        a first cross-member positioned between the first opening and the second opening, and
        a second cross-member positioned between the second opening and the third opening;
    a gas administration tube extending through the first cross-member such that the gas administration tube is positioned between the first opening and the second opening and comprising a first internal terminal end configured to be centrally positioned relative to the internal airway volume of the airway device such that the first terminal end is configured to be spaced apart from the internal-facing surfaces of the single continuous channel and a first port, the gas administration tube holding the first port in a fixed position relative to the airway device;
    a gas sampling tube extending through the second cross-member such that the gas sampling tube is positioned between the second opening and the third opening and comprising a second internal terminal end configured to be positioned centrally relative to the internal airway volume of the airway device such that the second internal terminal end is configured to be spaced apart from the internal-facing surfaces of the single continuous channel and a second port, the gas sampling tube holding the second port in a fixed position relative to the airway device;
    wherein the first internal terminal end is spaced apart from the body by a first distance and the second internal terminal end is spaced apart from the body by a second distance that is greater than the first distance, such that the second internal terminal end is positioned further into the airway device than the first internal terminal end,
    wherein the first cross-member and the second cross-member are configured not to extend within the single continuous channel, and
    wherein when the body is attached to the first end of the airway device, the single continuous channel of the airway device is unobstructed from the first internal terminal end of the gas administration tube and the second internal terminal end of the gas sampling tube.

2. The airway adjunct of claim 1, further comprising the airway device wherein the airway device comprises an oropharyngeal airway device.

3. The airway adjunct of claim 1, further comprising the airway device wherein the airway device comprises a nasopharyngeal airway device.

4. The airway adjunct of claim 1, further comprising a clamping tab integrated with the body, the clamping tab adapted to secure the body to a collar of the airway device.

5. The airway adjunct of claim 1, wherein:
    the gas administration tube comprises a first elbow bend and
    the gas sampling tube comprises a second elbow bend.

6. The airway adjunct of claim 1, wherein the first port and the second port are connected to the airway adjunct device via tubing connectors.

7. The airway adjunct of claim 1, wherein the first cross-member is oriented parallel to the second cross-member.

8. The airway adjunct of claim 1, wherein only a portion of the gas administration tube extending from the first cross-member to the first internal terminal end and a portion of the gas sampling tube extending from the second cross-member to the second internal terminal end extend from the body into the single continuous channel.

9. The airway adjunct of claim 8, wherein the portion of the gas administration tube extending from the first cross-member to the first internal terminal end defines a first axis and the portion of the gas sampling tube extending from the second cross-member to the second internal terminal end defines a second axis that is parallel to the first axis, and wherein a gap exists between the first axis and the second axis such that no other structure extending from body or from the airway device is positioned between the first axis and the second axis.

10. An airway adjunct adapted to secure to an airway device, the airway device having a first end, a second end opposite the first end, and an internal airway volume defined by a single continuous channel with one or more internal-facing surfaces extending from the first end to the second end, the airway adjunct comprising:
    a body that is configured to be removably coupled to the first end of the airway device, the body including
        a first surface positionable adjacent to the first end of the airway device,
        a second surface opposite the first surface,
        an opening extending through the body between the first surface and the second surface and configured to be in communication with the internal airway volume, the opening defining a first side and a second side opposite the first side,
a first cross-member extending from the first side of the opening to the second side of the opening, and
a second cross-member extending from the first side of the opening to the second side of the opening, the second cross-member being spaced apart from the first cross-member;
a gas administration tube comprising a first portion coupled to and in fluid communication with a second portion, the first portion extending through the first cross-member and oriented perpendicular to the first surface, the first portion defining a first internal terminal end configured to be positioned centrally relative to the internal airway volume of the airway device such that the first internal terminal end is configured to be spaced apart from the internal-facing surfaces of the single continuous channel, and the second portion oriented parallel to the second surface and defining a first port, the first port configured to be in communication with a gas source;
a gas sampling tube comprising a third portion coupled to and in fluid communication with a fourth portion, the third portion extending through the second cross-member and oriented perpendicular to the first surface, the third portion defining a second internal terminal end configured to be positioned centrally relative to the internal airway volume of the airway device such that the second internal terminal end is configured to be spaced apart from the internal-facing surfaces of the single continuous channel, and the fourth portion oriented parallel to the second surface and defining a second port, the second port configured to be in communication with a gas sampling machine;
wherein the first internal terminal end is spaced apart from the first surface by a first distance and the second internal terminal end is spaced apart from the first surface by a second distance that is greater than the first distance by such that the second internal terminal end is positioned further into the airway assembly than the first internal terminal end,
wherein the first cross-member and the second cross-member are configured not to extend within the single continuous channel, and
wherein when the body is attached to the first end of the airway device, the single continuous channel of the airway device is unobstructed from the first internal terminal end of the gas administration tube and the second internal terminal end of the gas sampling tube such that a carbon dioxide waveform is generated by the gas sampling machine.

11. The airway adjunct of claim 10, further comprising the airway device wherein the airway device comprises an oropharyngeal airway device or a nasopharyngeal airway device.

12. The airway adjunct of claim 10, further comprising a clamping tab integrated with the body, the clamping tab adapted to secure the body to a collar of the airway device.

13. The airway adjunct of claim 10, wherein the opening is a first opening and further comprising a second opening and a third opening, each of the second opening and the third opening extending through the body between the first surface and the second surface, and wherein the first cross-member extends between the first opening and the second opening, and the second cross-member extends between the second opening and the third opening.

14. The airway adjunct of claim 10, further comprising a clamping tab integrated with the body, the clamping tab adapted to secure the body to a collar of the airway device.

15. The airway adjunct of claim 10, wherein the gas administration tube is separated from the gas sampling tube by a gap that is unobstructed.

16. The airway adjunct of claim 10, wherein the first cross-member is oriented parallel to the second cross-member.

17. The airway adjunct of claim 10, wherein only a section of the first portion extending between the first surface and the first terminal end and a section of the third portion extending between the first surface and the second internal terminal end extend from the body into the single continuous channel.

18. An airway adjunct adapted to secure to an airway device, the airway device having a collar and a channel that extends from the collar to a distal end and that defines an internal airway volume defined by one or more internal-facing surfaces of the airway device extending from the collar to the distal end, the airway adjunct comprising:
a body that is configured to be removably coupled to the collar of the airway device, the body including
a first surface configured to abut the collar;
a second surface opposite the first surface;
a first opening extending through the body from the first surface to the second surface and configured to be in fluid communication with the internal airway volume,
a second opening extending through the body from the first surface to the second surface and configured to be in fluid communication with the internal airway volume,
a third opening extending through the body from the first surface to the second surface and configured to be in fluid communication with the internal airway volume,
a first cross-member positioned between the first opening and the second opening the first cross-member being spaced apart from the channel, and
a second cross-member positioned between the second opening and the third opening, the second cross-member being spaced apart from the channel;
a gas administration tube extending through the first cross-member such that the gas administration tube is positioned between the first opening and the second opening and comprising a first internal terminal end configured to be positioned centrally relative to the internal airway volume of the airway device such that the first terminal end is configured to be spaced apart from the internal-facing surfaces of the channel and a first port, the gas administration tube holding the first port in a fixed position relative to the airway device;
a gas sampling tube extending through the second cross-member such that the gas sampling tube is positioned between the second opening and the third opening and comprising a second internal terminal end configured to be positioned centrally relative to the internal airway volume of the airway device such that the second internal terminal end is configured to be spaced apart from the internal-facing surfaces of the channel and a second port, the gas sampling tube holding the second port in a fixed position relative to the airway device;
wherein the first internal terminal end is spaced apart from the body by a first distance and the second internal terminal end is spaced apart from the body by a second distance that is greater than the first distance, such that the second internal terminal end is positioned further into the airway device than the first internal terminal end, and wherein when the body is attached to the collar of the airway device, the single continuous channel of the airway device is unobstructed from the second internal terminal end to the second end of the airway device, wherein only a portion of the gas administration tube extending from the first cross-member to the first internal terminal end and a portion of the gas sampling tube extending from the second cross-member to the second internal terminal end extend from the body into the single continuous channel, and wherein the portion of the gas administration tube extending from the first cross-member to the first internal terminal end defines a first axis and the portion of the gas sampling tube extending from the second cross-member to the second internal terminal end defines a second axis that is parallel to the first axis, and wherein a gap exists between the first axis and the second axis such that no other structure extending from the body or from the airway device is positioned between the first axis and the second axis.

\* \* \* \* \*